US00PP12667P2

(12) United States Plant Patent
Noodelijk

(10) Patent No.: US PP12,667 P2
(45) Date of Patent: Jun. 4, 2002

(54) CHRYSANTHEMUM PLANT NAMED 'ROBSON'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/276,703

(22) Filed: Mar. 26, 1999

(51) Int. Cl.[7] ..... A01H 5/00
(52) U.S. Cl. ..... Plt./298
(58) Field of Search ..... Plt./298, 293, 287

(56) References Cited

PUBLICATIONS

UPOV–ROM GTITM Computer Database 2000/06, Dec. 8, 2000, GTI Jouve Retrieval Software, Citation for 'Robson'.*

* cited by examiner

*Primary Examiner*—Bruce R. Campell
*Assistant Examiner*—June Hwu

(57) ABSTRACT

A chrysanthemum plant named 'Robson' characterized by its medium sized bloom with red ray-florets and a greyed-yellow center.

2 Drawing Sheets

BACKGROUND OF THE INVENTION

'Robson' is a product of a breeding-program which had the objective of creating new chrysanthemum cultivars with an anemone type flower, a 7 week response and a medium plant height. The new plant of the present invention comprises a new and distinct cultivar of Chrysanthemum plant. 'Robson' is a seedling from a cross in a breeding program maintained under the control of inventor. The female parent is #90.602—unpatented—, an unnamed seedling not available to inventor for description. The male parent is unknown, being a mixed pollation of a group of male parents. The new and distinct cultivar was discovered and selected as a flowering plant within the progeny of the stated cross by Rob Noodelijk in a controlled environment (greenhouse) in Rijsenhout, Holland in May 1995. The first act of asexual reproduction of 'Robson' was accomplished when vegetative cuttings were taken from the initial selection in August 1995 in a controlled environment in Rijsenhout, Holland.

SUMMARY OF THE INVENTION

The present invention is a new and distinct variety of chrysanthemum bearing medium sized blooms with red ray-florets and a greyed-yellow center.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
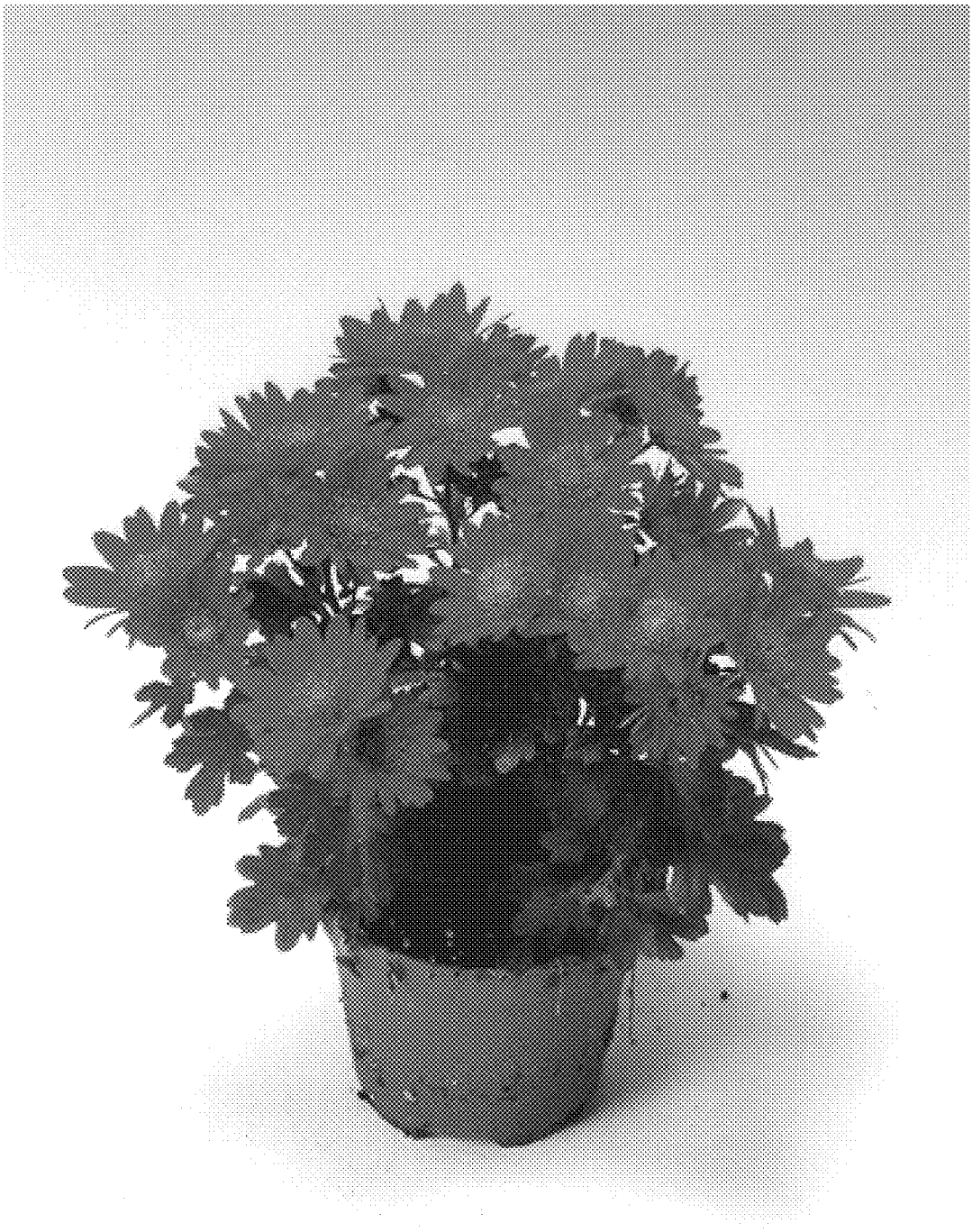
FIG. 1 shows a plant of the cultivar in full bloom.
Figure 2:
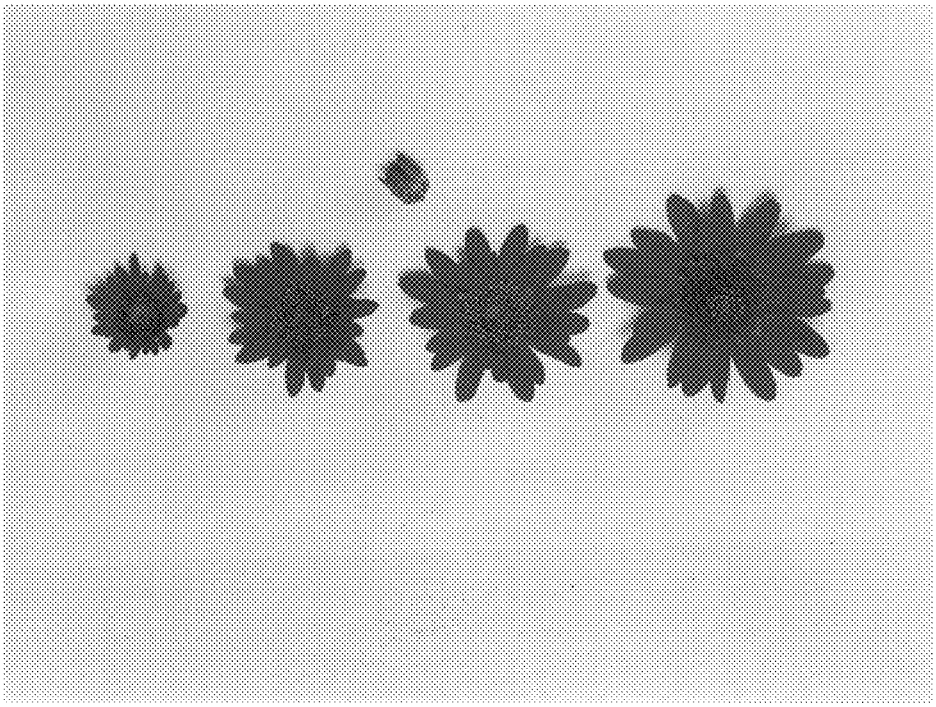
FIG. 2 shows the various stages of bloom of the new cultivar.
Figure 3:
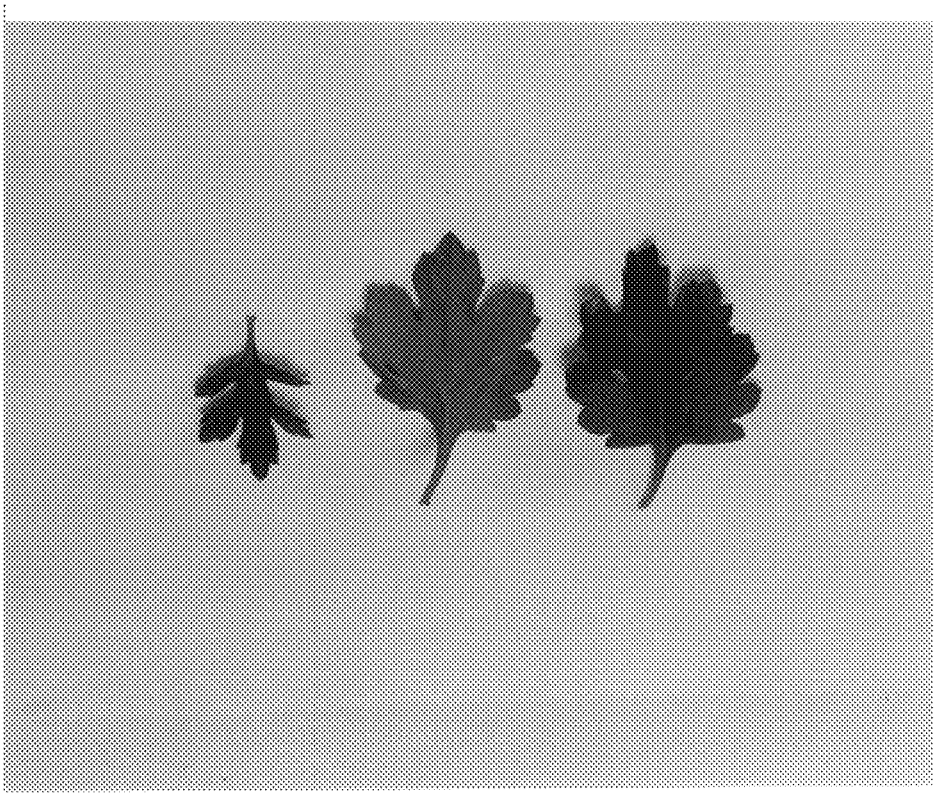
FIG. 3 shows the foliage of the new cultivar

This new variety of chrysanthemum is of the botanical classification *Dendranthema grandiflora*. The observations and measurements were gathered from plants grown in a greenhouse in Rijsenhout Holland in a photo-periodic controlled crop under conditions generally used in commercial practice. The photo-periodic response time in this crop was 48 days after an average of eight long days. After this long day period to flowering growth retardants were applied 6 times in an average dose of 1.5 gram/liter water. This new variety produces medium sized blooms with red ray-florets and a yellow-greyed center blooming on the plant for 5 weeks. This new variety of chrysanthemum has been found to retain its distinctive characteristics throughout successive ppropagations however the phenotype may vary significantly with variations in environment such as light intensity and temperature. To show the phenotype as described 'Robson' can be planted without assimilation lightning (high pressure sodium lamps) between week 50 and week 40 of the next year under greenhouse conditions in Holland. With assimilation lightning (minimum level 2500 lux) it can be planted year round under greenhouse conditions in Holland.

From the cultivars known to inventor the most similar existing cultivar in comparison to 'Robson' is 'Jasper' (U.S. Plant Pat. No. 9,155). When 'Jasper' and 'Robson' are being compared the following differences are noticed (in general terms): The differences of 'Jasper' and 'Robson' are: (1) Response time. (2) Habit of the plant and (3) Flower color.

The following is a description of the plant and characteristics that distinguish 'Robson' as a new and distinct variety.

The color designations are taken from the plant itself. Accordingly, any discrepancies between the color designations and the colors depicted in the photographs are due to photographic tolerances.

Table 1: Botanical Description of CULTIVAR 'Robson'

Bud:

*Size.*—Medium; cross-section 1.1 cm, height 1.0 cm.
*Outside color.*—Red-purple 42D.
*Involucral bracts.*—2 rows, length 8 mm., width 3 mm.
*Involucral bracts among disc-florets.*—Not present.
*Involucral bracts color.*—Green 138 B.

Bloom:
*Type.*—Anemone.
*Height.*—Medium high.
*Size.*—Medium.
*Fully expanded.*—5.5–6.0 cm.
*Borne* (*number of blooms per branch*).—Approx. 5 blooms per branch.
*Performance on the plant.*—5 weeks.
*Seeds.*—Not produced.
*Fragrance.*—Typical chrysanthemum.

Color:
*Center of the flower* (*disc-florets*).—Immature in the center 143B, to the outside 183B with 162A at the apex. Mature 44A with 162A at the apex.
*Color of upper surface of the majority of the ray-florets.*—Red 44B.
*Color of the lower surface of the majority of the ray-florets.*—Greyed-red 178D.
*Tonality from distance.*—A pot mum with red anemone flowers and a yellow-greyed center.
*Discoloration to color.*—Greyed-red 178D.

Ray florets:
*Texture.*—Upper and under side smooth.
*Number.*—20–22.
*Cross-section.*—Convex.
*Longitudinal axis of majority.*—Reflexing.
*Margin.*—Entire.
*Length of corolla tube.*—Short.
*Ray-floret length.*—2.5 cm.
*Ray-floret width.*—1.0 cm.
*Ratio length/width.*—Low.
*Shape of tip.*—Retuse and acute.

Disc florets:
*Disc diameter.*—Large (2.0–2.5 cm).
*Distribution of disc florets.*—Numerous and clearly visible at all stages of flowering.
*Type.*—Petaloid.
*Color.*—Greyed-red 183B with greyed-yellow 162A at the apex.
*Receptacle shape.*—Conical raised.

Reproductive organs:
*Stamen* (*present in disc florets only*).—Yellow-green 144A, thin, 2 mm in length.
*Pollen.*—No pollen.
*Pollen color.*—Not applicable.
*Styles* (*present in both ray and disc florets*).—Yellow-green 144A, thin.
*Style length.*—4 mm.
*Stigmas.*—Yellow-green 144A.
*Stigma width.*—2 mm.
*Ovaries.*—Enclosed in calyx.

Plant:
*Form.*—A pot mum meant for indoor use.
*Growth habit.*—Spreading.
*Growth rate.*—Slow.
*Height.*—19.0–22.0 cm.
*Width.*—25.0 cm.
*Stem color.*—Yellow-green 144A.
*Stem strength.*—Strong.
*Stem brittleness.*—Absent.
*Stem anthocyanin coloration.*—Present, a slight tint of greyed-purple 183 D.
*Length of lateral branch.*—From top to bottom 12.0 cm.
*Lateral branch color.*—Green 138 B.
*Lateral branch, attachment.*—Not strong, not weak.
*Branching* (*average number of lateral branches*).—Normal with 3–4 breaks after pinching.
*Peduncle length.*—3.0–3.5 cm.
*Peduncle color.*—Green 138 B.
*Flowering response* (*photo-periodic controlled crop, no natural growing*).—48 Days.

Foliage:
*Color.*—Upper side green 137 A. Under side green 138 A.
*Size.*—Medium, length 5.5 cm, width 5.0 cm.

Quantity (number per lateral branch): 5–8
*Shape.*—Ovate and pinnately lobed.
*Texture upper side.*—Fleshy.
*Texture under side.*—Pubescent.
*Ribs and veins upper side.*—Ribs and veins well developed.
*Ribs and veins upper side.*—Ribs and veins well developed.
*Venation arrangement.*—Palmate.
*Shape of the margin.*—Crenated.
*Shape of base of sinus between lateral lobes.*—Acute.
*Margin of sinus between lateral lobes.*—Converging.
*Shape of base.*—Truncate.
*Apex.*—Mucronate.
*Age.*—56 days.

TABLE 2

Differences with the comparison varieties

| | 'Robson' | 'Jasper' |
|---|---|---|
| Response time | 48 days | 54 days |
| Habit | Compact and spreading | Semi upright |
| Flower color | Intense red | Red-bronze |

I claim:

1. A new and distinct variety of chrysanthemum plant as described and illustrated.

* * * * *